US00PP12760P2

(12) United States Plant Patent
Meilland

(10) Patent No.: US PP12,760 P2
(45) Date of Patent: Jul. 2, 2002

(54) HYBRID TEA ROSE PLANT NAMED 'MEIJASPER'

(75) Inventor: Alain A. Meilland, Antibes (FR)

(73) Assignee: CP (Delaware), Inc., Wilmington, DE (US)

( * ) Notice: Subject to any disclaimer, the term of this patent is extended or adjusted under 35 U.S.C. 154(b) by 0 days.

(21) Appl. No.: 09/698,238

(22) Filed: Oct. 30, 2000

(51) Int. Cl.[7] ..... A01H 5/00
(52) U.S. Cl. ..... Plt./140
(58) Field of Search ..... Plt./140, 139, 130, Plt./151

(56) References Cited

PUBLICATIONS

UPOV–ROM GTITM Computer Database 2001/03, Jun. 21, 2001, GTI Jouve Retrieval Software, Citation for 'Meijasper'.*

Protection Des Obtentions Vegetales, Bulletin Officel du Comité de la Protection des Obtentions Végétales, Cover Page and pp. 334 and 340 (Sep. 10, 1999).

Protection Des Obtentions Vegetales, Bulletin Officiel du Comité de la Protection des Obtentions Végétales, Cover Page and p. 321 (Sep. 2001).

* cited by examiner

*Primary Examiner*—Bruce R. Campell
*Assistant Examiner*—June Hwu
(74) *Attorney, Agent, or Firm*—Burns, Doane, Swecker & Mathis, L.L.P.

(57) ABSTRACT

A new and distinct variety of Hybrid Tea rose plant is provided which abundantly forms attractive double red blossoms that are lightly perfumed. The blossoms are borne on long stems. The plant exhibits an erect growth habit, dense dark green semi-glossy foliage, and very good disease resistance. The attractive dark green foliage contrasts nicely with the red blossoms. The new variety is particularly well suited for use to produce cut flowers under greenhouse growing conditions.

1 Drawing Sheet

SUMMARY OF THE INVENTION

Figures 1, 2, 3, 4, 5, 6, 7, 8, 9, 10, 11, 12, 13, 14, 15, 16:
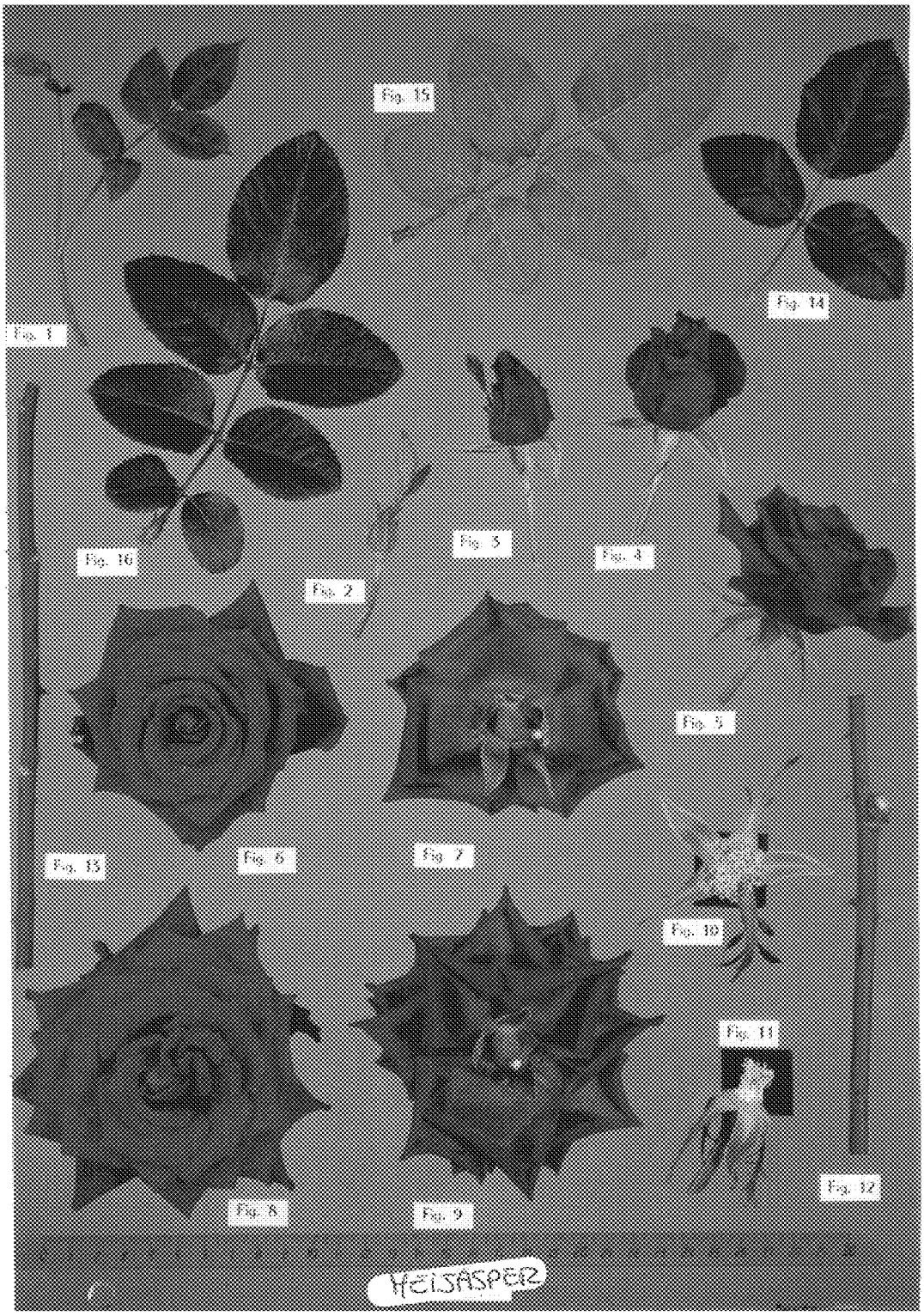

The new variety of *Rosa hybrida* Hybrid Tea rose plant was created by artificial pollination wherein two parents were crossed which previously had been studied in the hope that they would contribute the desired characteristics. The female parent (i.e., the seed parent) of the new variety was the 'Meibuito' variety (non-patented in the United States). The male parent (i.e., the pollen parent) was the 'Meibigoud' variety (U.S. Plant Pat. No. 9,308). The parentage of the new variety can be summarized as follows:

'Meibuito'×'Meibigoud'.

The seeds resulting from the above pollination were sown and small plants were obtained which were physically and biologically different from each other. Selective study resulted in the identification of a single plant of the new variety.

It was found that the new variety of Hybrid Tea rose plant of the present invention possesses the following combination of characteristics:

(a) exhibits an erect growth habit, (b) forms long stems, (c) abundantly forms double red blossoms that are lightly perfumed, (d) forms dense dark green semi-glossy foliage that contrasts well with the red blossoms, and (e) is particularly well suited for cut flower production under greenhouse growing conditions.

The disease resistance of the new variety is very good.

The new variety well meets the needs of the horticultural industry and can be used to advantage to form cut flowers when grown indoors.

The new variety has been found to undergo asexual propagation in France by a number of routes, including budding, grafting, and cuttage. Asexual propagation by the above-mentioned techniques in France has shown that the characteristics of the new variety are stable and are strictly transmissible by such asexual propagation from one generation to another.

The new variety has been named the 'Meijasper' variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and were observed during July while budded on *Rosa indica* understock and growing in greenhouses at Le Cannet des Maures, Var, France. Dimensions in centimeters are indicated at the botom of the photograph.

FIG. 1—illustrates a specimen of a young shoot;

FIG. 2—illustrates a specimen of a floral bud before the opening of the sepals;

FIG. 3—illustrates a specimen of a floral bud at the opening of the sepals;

FIG. 4—illustrates a specimen of a floral bud at the opening of the petals;

FIG. 5—illustrates a specimen of a flower in the course of opening;

FIG. 6—illustrates a specimen of an open flower—plan view—obverse;

FIG. 7—illustrates a specimen of an open flower—plan view—reverse;

FIG. 8—illustrates a specimen of a fully open flower—plan view—obverse;

FIG. 9—illustrates a specimen of a fully open flower—plan view—reverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of a main branch;

FIG. 13—illustrates a specimen of a flowering stem;

FIG. 14—illustrates a specimen of a leaf with three leaflets—plan view—upper surface;

FIG. 15—illustrates a specimen of a leaf with five leaflets—plan view—under surface; and FIG. 16—illustrates a specimen of a leaf with seven leaflets—plan view—upper surface.

DETAILED DESCRIPTION

The chart used in the identification of the colors is that of The Royal Horticultural Society (R.H.S. Colour Chart). The description is based on the observation of two year-old plants during July while budded on *Rosa indica* understock and growing in greenhouses at Le Cannet des Maures, Var, France. The coloration in more common terms precedes reference to the chart in some instances. Such terminology is to be accorded its ordinary dictionary significance.

Class: Hybrid tea.

Plant:

*Height.*—When pruned to a height of 85 cm, floral stems having a length of approximately 70 to 80 cm commonly are produced.

*Width.*—Approximately 60 to 70 cm on average.

*Habit.*—Erect.

Branches:

*Color.*—Young stems: near Green Group 138A with light anthocyanin coloration near Greyed-Red Group 178A. Adult wood: near Green Group 137B.

*Thorns.*—Size: immature thorns commonly measure approximately 3.5 to 4 cm in length on average, and mature thorns commonly measure approximately 4 to 6 cm in length on average. Quantity: moderately numerous (as illustrated). Color: near Yellow-Green Group 144A on young stems and near Greyed-Orange Group 170B on adult wood. Configuration: curved downwards on the upper surface and concave on the under surface.

Leaves:

*Stipules.*—Adnate, pectinate, approximately 1.2 to 1.4 cm in length on average, approximately 0.6 cm in width on average, and near Yellow-Green Group 146B in coloration.

*Petioles.*—Upper surface: slightly glandular and near Green Group 143A.

*Under surface*: Near Green Group 143A and bear a few prickles.

*Leaflets.*—Number: 3, 5 (most often), and 7. Shape: slightly ovate with an acute tip and a rounded base. Size: terminal leaflets commonly measure approximately 6 to 6.4 cm in length and approximately 4 to 4.4 cm in width on average. Serration: simle and regular (as illustrated). Texture: thick with a smooth and glossy upper surface. General appearance: dense, dark green, and semi-glossy. Color (young foliage): Upper surface: near Green Group 139A with light anthocyanin coloration near Greyed-Red Group 178A. Under surface: near Yellow-Green Group 147B with light anthocyanin coloration near Greyed-Red Group 178A. Color (adult foliage): Upper surface: near Green Group 139A. Under surface: near Greyed-Green Group 191A.

Inflorescence:

*Number of flowers.*—Usually one flower per stem.

*Peduncle.*—Long and rigid, without prickles, Yellow-Green Group 144A, and the length is approximately 13 cm on average.

*Sepals.*—Upper surface: medium green near Yellow-Green Group 144A, and three sepals commonly possess extensions having a significant length. Under surface: medium green, near Yellow-Green Group 144A, and three sepals commonly possess extensions of medium length (as illustrated). Length: commonly approximately 3 to 4 cm when without extensions and approximately 5 cm when extensions are present.

*Buds.*—Shape: conical. Size: medium. Color: sometimes with light antocyanin coloration near Greyed-Red Group 178A. Length: approximately 5 cm on average.

*Flower.*—Shape: flat cup-shaped, with slight petal undulation when opening begins, and with reflexed petal edges when fully open. Diameter: approximately 11 cm on average. Color (when opening begins): upper surface: Currant Red, near Red Group 46A, suffused with Cardinal Red, Red Group 53B. Under surface: Cardinal Red, near Red Group 53A. Color (when blooming): Upper surface: near Red Group 45B and lightly suffused with Currant Red, Red Group 46A. Under surface: Cardinal Red, near Red Group 53B. Color (at end of opening): Upper surface: near Red Group 45B and lightly suffused with Currant Red, Red Group 46A. Under surface: Cardinal Red, near Red Group 53C. Basal petal spot: small and near Yellow Group 9C on both surfaces. Fragrance: light. Lasting quality: very long, approximately 12 days on the plant and approximately 15 days when cut and placed in a vase. Petal shape: with an oboval base and a rounded tip. Petal texture: velvety. Petal number: approximately 35 to 40 on average. Petal size: commonly approximately 5 cm in length and approximately 5.5 cm in width on average. Petaloids: none observed. Petal drop: good, the petals detach cleanly. Stamen number: approximately 80 on average. Anthers: near Yellow-Orange Group 22A and approximately 0.4 cm in size on average. Filaments: near Red-Purple Group 58B and approximately 0.8 cm in length on average. Pollen: present and yellow in coloration. Pistils: approximately 150 on average. Stigmas: near Yellow-Orange Group 16C. styles: near White Group 155B in coloration, and approximately 1.2 cm in length on average. Receptacle: near Green Group 144B in coloration, and pitcher-shaped in longitudinal section. Hips: none observed.

Development:

*Vegetation.*—Medium vigor.

*Blooming.*—Abundant.

*Resistance to diseases.*—Very good with respect to common rose diseases when grown under greenhouse conditions.

*Susceptibilty to insects.*—No special susceptibility has been observed.

*Hardiness.*—Not evaluated since the variety is primarily intended for cut flower production under greenhouse growing conditions.

*Aptitude to bear fruit.*—None observed.

I claim:

1. A new and distinct variety of Hybrid Tea rose plant characterized by the following combination of characteristics:

(a) exhibits an erect growth habit, (b) forms long stems, (c) abundantly forms double red blossoms that are lightly perfumed, (d) forms dense dark green semi-glossy foliage that contrasts well with the red blossoms, and (e) is particularly well suited for cut flower production under greenhouse growing conditions;

substantially as herein shown and described.

* * * * *

HEISASPER